(12) United States Patent
Smith et al.

(10) Patent No.: US 11,629,133 B2
(45) Date of Patent: Apr. 18, 2023

(54) PERFLUOROAMINOOLEFINS AND METHODS OF MAKING AND USING THE SAME

(71) Applicant: 3M INNOVATIVE PROPERTIES COMPANY, St. Paul, MN (US)

(72) Inventors: Sean M. Smith, St. Paul, MN (US); Michael J. Bulinski, Stillwater, MN (US); Michael G. Costello, Afton, MN (US); Klaus Hintzer, Kastl (DE); Markus E. Hirscherg, Burgkirchen (DE); William M. Lamanna, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 17/055,498

(22) PCT Filed: May 10, 2019

(86) PCT No.: PCT/IB2019/053893
§ 371 (c)(1),
(2) Date: Nov. 13, 2020

(87) PCT Pub. No.: WO2019/220293
PCT Pub. Date: Nov. 21, 2019

(65) Prior Publication Data
US 2021/0221776 A1 Jul. 22, 2021

Related U.S. Application Data (60) Provisional application No. 62/671,500, filed on May 15, 2018.

(51) Int. Cl.
| | | |
|---|---|---|
| C07C 211/24 | (2006.01) | |
| C07D 265/30 | (2006.01) | |
| H01M 10/613 | (2014.01) | |
| C07D 207/10 | (2006.01) | |
| C07D 211/38 | (2006.01) | |
| C07D 223/04 | (2006.01) | |
| C08J 9/00 | (2006.01) | |
| C08J 9/12 | (2006.01) | |
| C08J 9/14 | (2006.01) | |
| F01K 25/02 | (2006.01) | |
| F28F 23/00 | (2006.01) | |
| H05K 7/20 | (2006.01) | |

(52) U.S. Cl.
CPC .......... *C07D 265/30* (2013.01); *C07C 211/24* (2013.01); *C07D 207/10* (2013.01); *C07D 211/38* (2013.01); *C07D 223/04* (2013.01); *C08J 9/0028* (2013.01); *C08J 9/125* (2013.01); *C08J 9/142* (2013.01); *F01K 25/02* (2013.01); *F28F 23/00* (2013.01); *H01M 10/613* (2015.04); *H05K 7/20236* (2013.01); *C07C 2601/10* (2017.05); *C07C 2601/16* (2017.05); *C07C 2601/18* (2017.05); *C08J 2203/162* (2013.01)

(58) Field of Classification Search
CPC ..................................................... C07C 211/24
See application file for complete search history.

(56) References Cited

U.S. PATENT DOCUMENTS

| 4,324,716 A | 4/1982 | Reischl |
| 2016/0312096 A1 | 10/2016 | Bulinski |

FOREIGN PATENT DOCUMENTS

| WO | WO 2015-095285 | 6/2015 | |
| WO | WO-2015095285 A1 * | 6/2015 | .......... A62D 1/0057 |
| WO | WO 2016-196240 | 12/2016 | |
| WO | WO 2018-039096 | 3/2018 | |

OTHER PUBLICATIONS

American Chemical Society. Chemical Abstract Service. RN 95883-93-5. First made available to Public/Entered into STN: Apr. 13, 1985. (Year: 1985).*
American Chemical Society. Chemical Abstract Service. RN 76944-18-8. First made available to Public/Entered into STN: Nov. 16, 1984. (Year: 1984).*
Abe, "The synthesis of perfluoro (N,N-dialkylcarbamoyl fluorides) by the reaction of perfluoro (N,N-dialkylmethylamines) with oleum", Journal of Fluorine Chemistry, Nov. 1989, vol. 45, No. 2, pp. 293-311.
Barnes, "Reactions Involving Fluoride Ion. Part 31.' Co-oligomers of Perfluoro-1-methyl- 1,3-diazacyclopent-2- and -3-ene", Journal of the Chemical Society, Perkin Transactions 1, 1985, pp. 53-56.
Dias, "Silver(I) and copper(I) complexes supported by fully fluorinated 1,3,5-triazapentadienyl ligands", Dalton Transactions, Sep. 2011, vol. 40, No. 34, pp. 8569-8580.
England, "Fluorovinylketones from perfluoropentene-2", Journal of Fluorine Chemistry, Jul. 1985, vol. 28, No. 04, pp. 417-423.
Gontar, "Preparation of Internal Perfluoroazomethines and Generation of Fluoroazanions from them", Russian Chemical Bulletin (Translated from Izvestiya Akademii Nauk SSSR, Seriya Khimicheskaya 1984, 1874-1877), Aug. 1984, vol. 33 No. 8, pp. 1711-1714.

(Continued)

*Primary Examiner* — John S Kenyon (57) ABSTRACT

Described herein is a perfluorinated aminoolefin compound of general formula (I): $CFY=CXN(R_f)CF_2R_f'$ where: (a) $R_f$ and $R_f'$ are (i) independently selected from a linear or branched perfluoroalkyl group having 1-8 carbon atoms, optionally comprising at least one catenated O or N atom, or (ii) bonded together to form a perfluorinated ring structure having 4-8 ring carbon atoms, optionally comprising at least one catenated O atom; and (b) X and Y are (i) independently selected from a perfluoroalkyl group having 1-4 carbon atoms, or (ii) bonded together to form a perfluorinated ring structure having 5-6 ring carbon atoms. Such compounds may be used in heat transfer, foam blowing or immersion cooling applications, or as a working fluid in a Rankine cycle, a coating or lubricant, or as a dielectric fluid. Also disclosed herein is a method for making such compounds.

20 Claims, 2 Drawing Sheets

(56) References Cited

OTHER PUBLICATIONS

Grinevskaja, "Reactivity of N-Perfluorpholynul Aza-Anion", Fluorine Notes, Apr. 2009, vol. 2, No. 63, 4 pages.
Klempner, "Handbook of Polymeric Foams and Foam Technology", 1st ed., Oxford University Press, 1991, Chapter 17, p. 407.
Ono, "Oligomerization reactions of perfluorovinylamines catalyzed by fluoride ions", Journal of Fluorine Chemistry, Mar. 1997, vol. 81, No. 2, pp. 163-168.
Petrov, "Reaction of Higher Perfluorinated Amines with Antimony Pentafluoride", Russian Chemical Bulletin (Translated from Izvestiya Akademii Nauk SSR, Seriya Khimicheskaya 1985, 1934-1935), Jan. 1985, vol. 34, No. 8, p. 1789.
Sarwar, "Secondary (polyfluoroalkyl)chloroamines: precursors to fluoroazaalkenes", Inorganic. Chemistry. Feb. 1990, vol. 29, No. 3, pp. 571-572.
International Search Report for PCT International Application No. PCT/IB2019/053893, dated Sep. 19, 2019, 4 pages.

* cited by examiner

PERFLUOROAMINOOLEFINS AND METHODS OF MAKING AND USING THE SAME

CROSS REFERENCE TO RELATED APPLICATIONS

This application is a national stage filing under 35 U.S.C. § 371 of PCT/IB2019/053893, filed May 10, 2019, which claims the benefit of Provisional Application No. 62/671,500, filed May 15, 2018, the disclosures of which are incorporated by reference in their entirety herein.

TECHNICAL FIELD

The present disclosure relates to a perfluorinated aminoolefin and methods of making and using the same.

SUMMARY

There continues to be a need for inert fluorinated fluids which have low global warming potential while providing high thermal stability, nonflammability, good solvency, and a wide operating temperature range to meet the requirements of various applications. Those applications include, but are not restricted to, heat transfer, immersion cooling, coatings/lubricants, dielectric fluids, and foams.

In one aspect, a perfluorinated aminoolefin compound is provided. The perfluorinated aminoolefin compound is represented by the following general formula (I): $CFY=CXN(R_f)CF_2R_f'$ where:
  (a) $R_f$ and $R_f'$ are (i) independently selected from a linear or branched perfluoroalkyl group having 1-8 carbon atoms, optionally comprising at least one catenated O or N atom, or (ii) bonded together to form a perfluorinated ring structure having 4-8 ring carbon atoms, optionally comprising at least one catenated O atom; and
  (b) X and Y are (i) independently selected from a perfluoroalkyl group having 1-4 carbon atoms, or (ii) bonded together to form a perfluorinated ring structure having 5-6 ring carbon atoms.

In one aspect, an immersion cooling system is provided. The system comprising: (A) a housing having an interior space; (B) a heat-generating component disposed within the interior space; and (C) a working fluid liquid disposed within the interior space such that the heat-generating component is in contact with the working fluid liquid; wherein the working fluid comprises the perfluorinated aminoolefin of general formula (I) above.

In another aspect, a thermal management system for a lithium-ion battery pack is provided, the system comprising: (A) a lithium-ion battery pack; and (B) a working fluid in thermal communication with the lithium-ion battery pack, wherein the working fluid comprises the perfluorinated aminoolefin compound according to general formula (I) above.

In one aspect, a method of making a perfluorinated aminoolefin is provided. The method comprising: contacting a perfluorinated imine with a perfluoroolefin in the presence of a metal fluoride catalyst, wherein the perfluorinated imine is of general formula (II) $RfN=CFRf'$ wherein Rf and Rf' are (i) independently selected from a linear or branched perfluoroalkyl group having 1-8 carbon atoms, optionally comprising at least one catenated O or N atom, or (ii) bonded together to form a perfluorinated ring structure having 4-8 ring carbon atoms, optionally comprising at least one catenated O atom and the perfluoroolefin of general formula (III) $CXF=CFY$ wherein X and Y are (i) independently selected from a perfluoroalkyl group having 1-4 carbon atoms, or (ii) bonded together to form a perfluorinated ring structure having 5-6 ring carbon atoms.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term

"a", "an", and "the" are used interchangeably and mean one or more; and

"and/or" is used to indicate one or both stated cases may occur, for example A and/or B includes, (A and B) and (A or B);

"alkyl" refers to a monovalent group that is a radical of an alkane, which is a saturated hydrocarbon. The alkyl group can be linear, branched, cyclic or combinations thereof;

"catenated" means an atom other than carbon (for example, oxygen or nitrogen) that is bonded to at least two carbon atoms in a carbon chain (linear or branched or within a ring) so as to form a carbon-heteroatom-carbon linkage; and "perfluorinated" means a group or a compound wherein all hydrogen atoms in the C—H bonds have been replaced by C—F bonds.

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

As used herein, "comprises at least one of" A, B, and C refers to element A by itself, element B by itself, element C by itself, A and B, A and C, B and C, and a combination of all three.

For purposes of the present disclosure, it is to be appreciated that the unsaturated fluorinated compounds disclosed herein may include the E isomer, the Z isomer, or a mixture of the E and Z isomers, irrespective of what is depicted in any of the general formulas or chemical structures.

Specialty materials, such as perfluorocarbons (PFCs), perfluorinated tertiary-amines (PFAs), perfluoropolyethers (PFPEs) and hydrofluorocarbons (HFCs), have combinations of properties that make them useful in applications such as, for example, electrical power generation and transmission, reactive metal casting, heat transfer for thermal management in electronic devices and batteries, thermal runaway protection for batteries, heat transfer in semiconductor manufacturing, semiconductor cleaning, and for use as foam blowing additives. These specialty materials generally have low flammability or are nonflammable, have very good thermal and chemical stability, are not ozone depleting, and in addition have properties needed for the applications, such as low electrical conductivity, high dielectric strength, high heat capacity, high heat of vaporization, high volatility, very low residue after drying, noncorrosive and/or low mutual solubility in organics.

The good thermal and chemical stability of PFCs, PFPEs, and HFCs also translates into long atmospheric lifetimes and high global warming potentials (GWPs). As a result, some of these materials are included in the list of greenhouse gases, which were subject to the Kyoto Protocol and subsequent regulations to control emissions. The objective of these regulations is to reduce the emission of greenhouse gases from processes using greenhouse gases and to reduce or minimize their impact on climate change. Capture of emissions and/or destroying them before emission has proven to be both difficult and costly. Replacement materials with more environmentally acceptable properties are needed for these applications.

Two groups of advanced materials, hydrofluoroethers (HFEs) and fluoroketones (FKs), have been shown to satisfactorily replace high GWP materials in a few applications such as fire extinguishing agents and precision cleaning, immersion cooling, and coating of electronics and in processes used to manufacture them. However, these materials cannot act as replacements in all applications due to chemical stability limitations. In some applications, HFE and FK chemical compositions are not suitable. For example, the carbon backbone of HFEs are likely to form conducting carbonaceous deposits if used as a dielectric insulating gas in power transmission equipment and cause equipment failure. And, for use as polyurethane foam blowing additives, HFEs and FKs are generally too reactive with the polyol/amine components of the foam formulation to be useful.

As a result, additional substitute materials are desired that will perform satisfactorily and safely in certain applications. These new substitute materials also should have much shorter atmospheric lifetimes and lower GWPs compared to the materials they replace to be environmentally acceptable.

The perfluorinated aminoolefins disclosed herein have many of the properties that are desired for application in, for example, insulating dielectric gases for electrical power generation and transmission, protective cover agents for reactive molten metal casting, direct contact immersion cooling and heat transfer, semiconductor cleaning, working fluids for organic Rankine cycle equipment, and for use as foam blowing additives.

The perfluorinated aminoolefin of the present disclosure (herein referred to interchangeably as a compound of the present disclosure) are of the general formula (I)

$$CFY=CXN(Rf)CF_2Rf' \quad (I)$$

where:
Rf and Rf' are (i) independently selected from a linear or branched perfluoroalkyl group having 1-8 carbon atoms, optionally comprising at least one catenated O or N atom, or (ii) bonded together to form a perfluorinated ring structure having 4-8 ring carbon atoms, optionally comprising at least one ether linkage; and
X and Y are (i) independently selected from a perfluoroalkyl group having 1-4 carbon atoms, or (ii) bonded together to form a perfluorinated ring structure having 5-6 ring carbon atoms.

In one embodiment, Rf and Rf' are independently selected from a linear or branched perfluoroalkyl group having 1-8 carbon atoms, 2-6 carbon atoms, or even 2-4 carbon atoms, optionally comprising at least one catenated oxygen atom (or ether linkage). Exemplary Rf and Rf' groups include: —$CF_3$; —$(CF_2)_nCF_3$ where n is 1, 2, 3, 4, 5, or 6; $C(CF_3)_2CF_3$, and —$CF(CF_3)CF_3$.

In another embodiment, Rf and Rf' are connected to form a ring structure moiety comprising a total of 4 to 8 carbon atoms in addition to optional catenary heteroatoms such as oxygen or nitrogen. The ring structure moiety may comprise a 4-, 5a-, or 6-membered ring. The ring which is made up of the nitrogen atom from the carboximidate may also include an oxygen atom (ether linkage) in the ring. In addition, or alternatively, the ring may comprise pendent perfluorinated alkyl groups, which may optionally comprise at least one catenated atom selected from oxygen, nitrogen, or combinations thereof. Exemplary ringed structures include: 5-membered rings such as pyrroles, and 6-membered rings such pyridines, and 6-membered rings comprising a catenated oxygen (such as 1,4-oxazines).

In one embodiment, X and Y are independently selected from a linear or branched perfluoroalkyl group having 1-4 carbon atoms. Exemplary X and Y groups include: —$CF_3$; —$(CF_2)_nCF_3$ where n is 1, 2, or 3; $C(CF_3)_2CF_3$, and —$CF(CF_3)CF_3$.

In another embodiment, X and Y are connected to form a 5- or 6-membered perfluorinated ring structure.

Exemplary compounds of the present disclosure include:

-continued

-continued

As used herein, the "F" within a ring structure means that each carbon within the ring structure is fluorinated and the wavy line in the isomeric structures above represents that the structure can be cis or trans in nature.

In one embodiment, the compound of the present disclosure can be prepared by contacting a perfluorinated imine of general formula II, $CFR_f'=NR_f$, with a perfluoroolefin of general formula III, $CFX=CFY$, in the presence of a metal fluoride catalyst, [M]F; where X, Y, Rf and Rf' are the same as defined above. An exemplary reaction is shown below:

In one embodiment, the perfluorinated imine is selected from a perfluorinated imidoyl fluoride, a perfluorinated oxazine, or a perfluorinated pyrrole compound. Such compounds are commercially available or can be synthesized using methods such as those disclosed in H. V. Rasika Dias et al. in Dalton Transactions, 2011, vol. 40, page 8569-8580; T. Abe, et al. in J. Fluorine Chem. 1989, vol. 45, pages 293-311, and A. F. Gontar, et al. in Izvestiya Akademii Nauk SSSR, Seriya Khimicheskaya 1984, vol. 33 issue 8, pages 1711-1714.

Exemplary perfluorinated imines include:

In one embodiment, the perfluoroolefin is of general formula III CFX=CFY, wherein X and Y are defined above. Such perfluoroolefins may be commercially available or synthesized using techniques known in the art.

Exemplary perfluoroolefins include:

Metal fluoride catalysts are known in the art and can include CsF, KF, AlF$_3$, MgF$_2$, CaF$_2$, SrF$_2$, BaF$_2$, and combinations thereof. Because the metal fluoride catalyst is regenerated during the reaction, typically low amount (e.g., less than 50, 40, 30 or even 20 mole % versus the perfluorinated olefin) are used.

The perfluoroolefin of formula III and the perfluorinated imine of formula II are combined in the presence of the metal fluoride catalyst and heated, whether it is to ambient temperature or higher temperatures such as temperatures greater than 40, 50, or 70° C.

The ratio of the perfluoroolefin of formula III and the perfluorinated imine of formula II is typically less than 0.85 to 1, or even less than 0.70 to 1.

A solvent may be used to solubilize the reactants for a reaction to occur. Useful solvents include organic solvents, such as polar aprotic solvents. Polar aprotic solvents include, ethers (such as bis(2-methoxyethyl) ether and tetraethylene glycol dimethyl ether), nitriles (such as acetonitrile, adiponitrile, and benzonitrile), dimethylsulfoxide, N-methylpyrrolidinone (NMP), N,N-dimethylformamide (DMF), and tetrahydrothiophene-1,1-dioxide (sulfolane), which can be used individually or as a mixture.

In one embodiment, the resulting fluorinated compounds from the reaction can be purified to isolate the desired perfluorinated aminoolefin. Purification can be done by conventional means including distillation, absorption, extraction, chromatography and recrystallization. The purification can be done to isolate the compound of the present disclosure (in all of its stereoisomeric forms) from impurities, such as starting materials, byproducts, etc. The term "purified form" as used herein means the compound of the present disclosure is at least 75, 80, 85, 90, 95, 98, or even 99 wt % pure.

The compounds of the present disclosure have good environmental properties as well as having good performance attributes, such as non-flammability, chemical inertness, high thermal stability, good solvency, etc.

In one embodiment, the compound of the present disclosure may have a low environmental impact. In this regard, the compounds of the present disclosure may have a global warming potential (GWP) of less than 1000, 700, or even 500. As used herein, GWP is a relative measure of the global warming potential of a compound based on the structure of the compound. The GWP of a compound, as defined by the Intergovernmental Panel on Climate Change (IPCC) in 1990 and updated in 2007, is calculated as the warming due to the release of 1 kilogram of a compound relative to the warming due to the release of 1 kilogram of $CO_2$ over a specified integration time horizon (ITH).

$$GWP_i(t') = \frac{\int_0^{ITH} a_i[C(t)]dt}{\int_0^{ITH} a_{CO_2}[C_{CO_2}(t)]dt} = \frac{\int_0^{ITH} a_i C_{oi} e^{-t/\tau_i} dt}{\int_0^{ITH} a_{CO_2}[C_{CO_2}(t)]dt}$$

In this equation a$_i$ is the radiative forcing per unit mass increase of a compound in the atmosphere (the change in the flux of radiation through the atmosphere due to the IR absorbance of that compound), C is the atmospheric concentration of a compound, $\tau$ is the atmospheric lifetime of a compound, t is time, and i is the compound of interest. The commonly accepted ITH is 100 years representing a compromise between short-term effects (20 years) and longer-term effects (500 years or longer). The concentration of an organic compound, i, in the atmosphere is assumed to follow pseudo first order kinetics (i.e., exponential decay). The concentration of $CO_2$ over that same time interval incorporates a more complex model for the exchange and removal of $CO_2$ from the atmosphere (the Bern carbon cycle model).

In one embodiment, the compounds of the present disclosure have atmospheric lifetime of less than 10 years, or even less than 5 years when tested following the Atmospheric Lifetime Test Method disclosed in the Example Section.

Non-flammability can be assessed by using standard methods such as ASTM D-3278-96 e-1 "Standard Test Method for Flash Point of Liquids by Small Scale Closed-Cup Apparatus". In one embodiment, the compound of the present disclosure is non-flammable based on closed-cup flashpoint testing following ASTM D-3278-96 e-1.

In one embodiment, the compound of the present disclosure is non-bioaccumulative in animal tissues. For example, some compounds of the present disclosure may provide low log $K_{ow}$ values, indicating a reduced tendency to bioaccumulate in animal tissues, where $K_{ow}$ is the octanol/water partition coefficient, which is defined as the ratio of the given compound's concentration in a two-phase system comprising an octanol phase and an aqueous phase. In one embodiment, the log $K_{ow}$ value is less than 7, 6, 5, or even 4.

In one embodiment, the compound of the present disclosure is thermally stable, meaning that when the compound is heated, there is minimal loss of purity. For example, if the perfluorinated aminoolefin is heated at 60° C. for 24 hours, there is a loss of less than 5%, 3%, or even 1%. In one embodiment, if the perfluorinated aminoolefin is heated at 100, 120 or even 150° C., for 24 hours, there is a loss of less than 5%, 3%, or even 1%.

In one embodiment, the compound of the present disclosure has a wide operating range. The useful liquid range of a compound of the present disclosure is between its pour point and its boiling point. A pour point is the lowest temperature at which the compound is still able to be poured. The pour point can be determined, for example, by ASTM D 97-16 "Standard Test Method for Pour Point of Petroleum Products". In one embodiment, the compound of the present disclosure has a pour point of less than 0° C., –20° C., –30° C., –40° C. or even –60° C. In one embodiment, the compound of the present disclosure has a boiling point of at least 100° C., 150° C., or even 200° C. at atmospheric pressure. In some embodiments the compound of the present disclosure has a boiling point from about 50° C. to about 200° C., about 100° C. to about 150° C., or even about 110° C. to about 130° C.

In one embodiment, the compounds of the present disclosure have a dielectric constant of less than 2.3, 2.2, 2.1, or even 2.0 as determined by ASTM D 150 measured at 1 kHz (kilohertz).

Heat Transfer

In some embodiments, the compounds of the present disclosure may be used in a heat transfer apparatus for transferring heat to or from the device.

The provided apparatus for heat transfer may include a device. The device may be a component, work-piece, assembly, etc. to be cooled, heated or maintained at a predetermined temperature or temperature range. Such devices include electrical components, mechanical components and optical components. Examples of devices of the present disclosure include, but are not limited to microprocessors, wafers used to manufacture semiconductor devices, power control semiconductors, electrical distribution switch gear, power transformers, circuit boards, multi-chip modules, packaged and unpackaged semiconductor devices, lasers, chemical reactors, fuel cells, and electrochemical cells. In some embodiments, the device can include a chiller, a heater, or a combination thereof.

The provided apparatus may include a mechanism for transferring heat. The mechanism may include a heat transfer fluid. The heat transfer fluid may include one or more perfluorinated aminoolefin compounds of formula (I). Heat may be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism.

The heat transfer mechanism may include facilities for managing the heat-transfer fluid, including, but not limited to pumps, valves, fluid containment systems, pressure control systems, condensers, heat exchangers, heat sources, heat sinks, refrigeration systems, active temperature control systems, and passive temperature control systems. Examples of suitable heat transfer mechanisms include, but are not limited to, temperature controlled wafer chucks in plasma enhanced chemical vapor deposition (PECVD) tools, temperature-controlled test heads for die performance testing, temperature-controlled work zones within semiconductor process equipment, thermal shock test bath liquid reservoirs, and constant temperature baths. In some systems, such as etchers, ashers, PECVD chambers, vapor phase soldering devices, and thermal shock testers, the upper desired operating temperature may be as high as 170° C., as high as 200° C., or even as high as 230° C.

The provided apparatus can also include refrigeration systems, cooling systems, testing equipment and machining equipment. In some embodiments, the provided apparatus can be a constant temperature bath or a thermal shock test bath.

In other aspects, a method of transferring heat is provided that includes providing a device and transferring heat to or from the device using a mechanism. The mechanism can include a heat transfer fluid such as the perfluorinated aminoolefin compounds of formula (I).

Organic Rankine-Cycle Working Fluid

In some embodiments, the compound of the present disclosure may be used as a working fluid to convert thermal energy into mechanical energy in a Rankine cycle. The apparatus may further include a heat source to vaporize the working fluid and form a vaporized working fluid, a turbine through which the vaporized working fluid is passed thereby converting thermal energy into mechanical energy, a condenser to cool the vaporized working fluid after it is passed through the turbine, and a pump to recirculate the working fluid.

Figure 1:
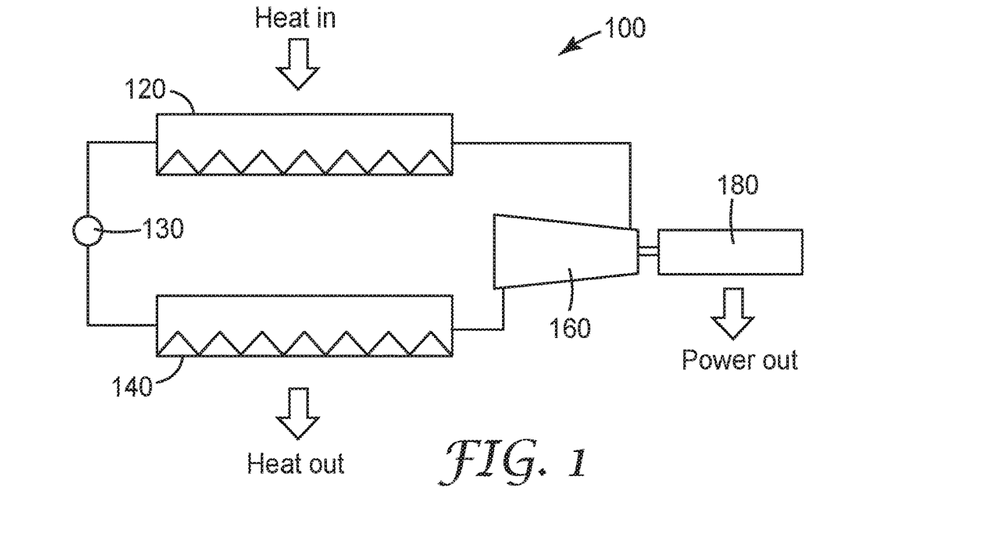
FIG. 1 is a schematic illustration of an apparatus for converting thermal energy into mechanical energy in a Rankine cycle.

A process for converting thermal energy into mechanical energy in a Rankine cycle is provided that includes a working fluid that includes one or more perfluorinated aminoolefin compounds of formula (I). Referring to FIG. 1, a typical Rankine cycle system 100 is shown that includes an evaporator/boiler 120 which receives heat from an external source. The evaporator/boiler 120 vaporizes an organic Rankine working fluid contained within the closed system 100. The Rankine cycle system 100 also includes a turbine 160 which is driven by the vaporized working fluid in the system and is used to turn a generator 180 thus producing electrical power. The vaporized working fluid is then channeled through a condenser 140 removing excess heat and reliquifying the liquid working fluid. A power pump 130 increases the pressure of the liquid leaving the condenser 140 and also pumps it back into the evaporator/boiler 120 for further use in the cycle. Heat released from the condenser 140 can then be used for other purposes including driving a secondary Rankine system (not shown).

Figure 2:
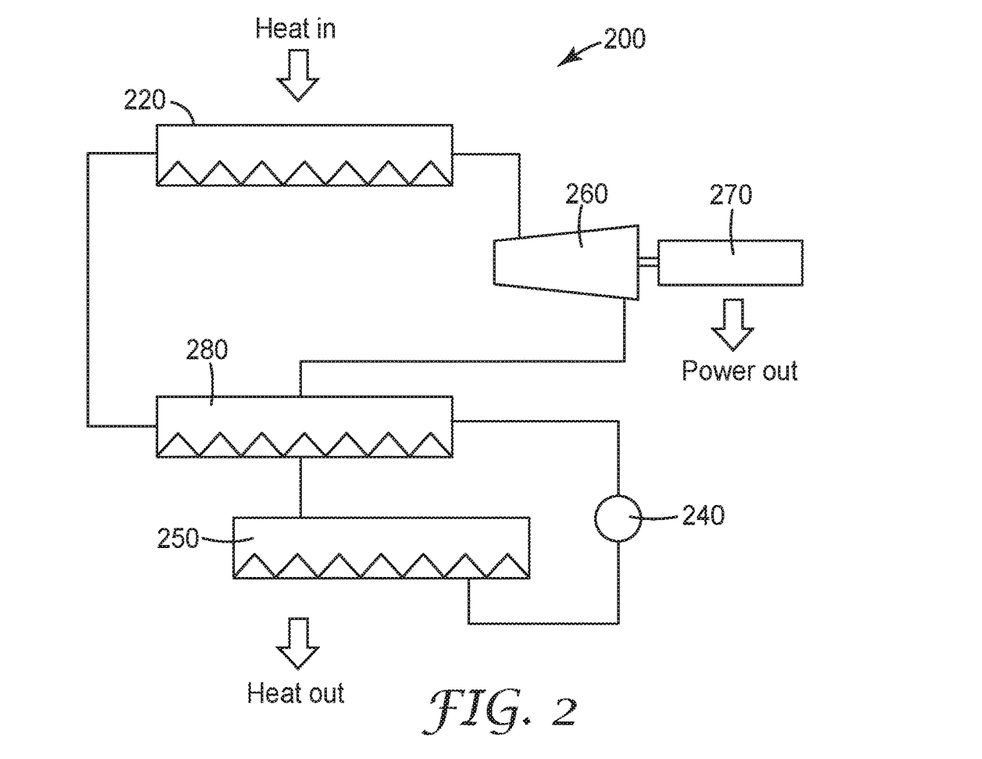
FIG. 2 is a schematic illustration of a Rankine cycle apparatus that includes a recuperator.

It is generally desirable to have fluids with saturated vapor curves that are either isentropic or have a positive slope on a temperature-entropy diagram. In cases where the saturated vapor curve has a positive slope, Rankine cycle efficiency can be improved through the use of an extra heat exchanger (or recuperator) to recover heat from vapor exiting the expander and using the recovered heat to pre-heat liquid coming out of the pump. FIG. 2 is an illustration of Rankine cycle system that includes a recuperator.

Referring to FIG. 2, a Rankine cycle system 200 is shown that includes an evaporator/boiler 220 which receives heat from an external source. The evaporator/boiler 220 vaporizes an organic Rankine working fluid contained within the closed system 200. The Rankine cycle system 200 also includes a turbine 260 which is driven by the vaporized working fluid in the system and is used to turn a generator 270 thus producing electrical power. The vaporized working fluid is then channeled through a recuperator 280 removing some excess heat and from there to the condenser 250, where the working fluid condenses back to liquid. A power pump 240 increases the pressure of liquid leaving the condenser 250 and also pumps it back into the recuperator 280, where it is preheated before going back into the evaporator/boiler 220 for further use in the cycle. Heat released from the condenser 250 can then be used for other purposes including driving a secondary Rankine system (not shown).

In some embodiments, the present disclosure relates to a process for converting thermal energy into mechanical energy in a Rankine cycle. The process may include using a heat source to vaporize a working fluid that includes one or more perfluorinated aminoolefin compounds of formula (I) to form a vaporized working fluid. In some embodiments, the heat is transferred from the heat source to the working fluid in an evaporator or boiler. The vaporized working fluid may be pressurized and can be used to do work by expansion. The heat source can be of any form such as from fossil fuels, e.g., oil, coal, or natural gas. Additionally, in some embodiments, the heat source can come from nuclear power, solar power, or fuel cells. In other embodiments, the heat can be "waste heat" from other heat transfer systems that would otherwise be lost to the atmosphere. The "waste heat," in some embodiments, can be heat that is recovered from a second Rankine cycle system from the condenser or other cooling device in the second Rankine cycle.

An additional source of "waste heat" can be found at landfills where methane gas is flared off. Other sources of "waste heat" that can be useful in the provided processes are geothermal sources and heat from other types of engines such as gas turbine engines that give off significant heat in their exhaust gases and to cooling liquids such as water and lubricants.

In the provided process, the vaporized working fluid may be expanded though a device that can convert the pressurized working fluid into mechanical energy. In some embodiments, the vaporized working fluid is expanded through a turbine which can cause a shaft to rotate from the pressure of the vaporized working fluid expanding. The turbine can then be used to do mechanical work such as, in some embodiments, operate a generator, thus generating electricity. In other embodiments, the turbine can be used to drive belts, wheels, gears, or other devices that can transfer mechanical work or energy for use in attached or linked devices.

After the vaporized working fluid has been converted to mechanical energy the vaporized (and now expanded) working fluid can be condensed using a cooling source to liquefy for reuse. The heat released by the condenser can be used for other purposes including being recycled into the same or another Rankine cycle system, thus saving energy. Finally, the condensed working fluid can be pumped by way of a pump back into the boiler or evaporator for reuse in a closed system.

Foam Blowing

In one embodiment, the perfluorinated aminoolefins disclosed herein can be used as nucleating agents in the production of polymeric foams and in particular in the production of polyurethane foams and phenolic foams. In this regard, in some embodiments, the present disclosure is directed to a foamable composition that includes one or more blowing agents, one or more foamable polymers or precursor compositions thereof, and one or more nucleating agents that include a perfluorinated aminoolefin compound of formula (I).

In some embodiments, a variety of blowing agents may be used in the provided foamable compositions including liquid or gaseous blowing agents that are vaporized in order to foam the polymer or gaseous blowing agents that are generated in situ in order to foam the polymer. Illustrative examples of blowing agents include hydrochlorofluorocarbons (HCFCs), hydrofluorocarbons (HFCs), hydrochlorocarbons (HCCs), iodofluorocarbons (IFCs), hydrofluoroolefins (HFO), hydrocarbons, and hydrofluoroethers (HFEs). The blowing agent for use in the provided foamable compositions can have a boiling point of from about −45° C. to about 100° C. at atmospheric pressure. Typically, at atmospheric pressure the blowing agent has a boiling point of at least about 15° C., more typically between about 20° C. and about 80° C. Further illustrative examples of blowing agents that can be used include aliphatic and cycloaliphatic hydrocarbons having about 5 to about 7 carbon atoms, such as n-pentane and cyclopentane, esters such as methyl formate, HFO's such as $CF_3CH=CHCF_3$, $CF_3CH=CHF$; HFCs such as $CF_3CF_2CHFCHFCF_3$, $CF_3CH_2CF_2H$, $CF_3CH_2CF_2CH_3$, $CF_3CF_2H$, $CH_3CF_2H$ (HFC-152a), $CF_3CH_2CH_2CF_3$ and $CHF_2CF_2CH_2F$, HCFCs such as $CH_3CCl_2F$, $CF_3CHCl_2$, and $CF_2HCl$, HCCs such as 2-chloropropane, and IFCs such as $CF_3I$, and HFEs such as $C_4F_9OCH_3$. In certain formulations $CO_2$ generated from the reaction of water with foam precursor such as an isocyanate can be used as a blowing agent.

In various embodiments, the provided foamable composition may also include one or more foamable polymers or a precursors composition thereof. Foamable polymers suitable for use in the provided foamable compositions include, for example, polyolefins, e.g., polystyrene, poly(vinyl chloride), and polyethylene. Foams can be prepared from styrene polymers using conventional extrusion methods. The blowing agent composition can be injected into a heat-plastified styrene polymer stream within an extruder and admixed therewith prior to extrusion to form foam. Representative examples of suitable styrene polymers include, for example, the solid homopolymers of styrene, α-methylstyrene, ring-alkylated styrenes, and ring-halogenated styrenes, as well as copolymers of these monomers with minor amounts of other readily copolymerizable olefinic monomers, e.g., methyl methacrylate, acrylonitrile, maleic anhydride, citraconic anhydride, itaconic anhydride, acrylic acid, N-vinylcarbazole, butadiene, and divinylbenzene. Suitable vinyl chloride polymers include, for example, vinyl chloride homopolymer and copolymers of vinyl chloride with other vinyl monomers. Ethylene homopolymers and copolymers of ethylene with, e.g., 2-butene, acrylic acid, propylene, or butadiene may also be useful. Mixtures of different types of polymers can be employed.

Precursors of foamable polymers suitable for use in the provided foamable compositions may include, for example, precursors of phenolic polymers, silicone polymers, and isocyanate-based polymers, e.g., polyurethane, polyisocyanurate, polyurea, polycarbodiimide, and polyimide. Typically, precursors of isocyanate-based polymers are utilized as the blowing agent for preparing polyurethane or polyisocyanurate foams.

Polyisocyanates suitable for use in the provided foamable compositions include aliphatic, alicyclic, arylaliphatic, aromatic, or heterocyclic polyisocyanates, or combinations thereof. Any polyisocyanate which is suitable for use in the production of polymeric foams can be utilized. For example, aromatic diisocyanates such as toluene and diphenylmethane diisocyanates in pure, modified, or crude form may be employed. MDI variants (diphenylmethane diisocyanate modified by the introduction of urethane, allophanate, urea, biuret, carbodiimide, uretonimine, or isocyanurate residues) and the mixtures of diphenylmethane diisocyanates and oligomers thereof known in the art as crude or polymeric MDI (polymethylene polyphenylene polyisocyanates) may be useful. Representative examples of suitable polyisocyanates include, for example, ethylene diisocyanate, 1,4-tetramethylene diisocyanate, 1,6-hexamethylene diisocyanate, trimethyl hexamethylene diisocyanate, 1,12-dodecane diisocyanate, cyclobutane-1,3-diisocyanate, cyclohexane-1,3- and -1,4-diisocyanate (and mixtures of these isomers), diisocyanato-3,3,5-trimethyl-5-isocyanatomethyl cyclohexane, 2,4- and 2,6-toluene diisocyanate (and mixtures of these isomers), diphenylmethane-2,4'- and/or -4,4'-diisocyanate, naphthalene-1,5-diisocyanate, the reaction products of four equivalents of the aforementioned isocyanate-containing compounds with compounds containing two isocyanate-reactive groups, triphenyl methane-4,4',4''-triisocyanate, polymethylene polyphenylene polyisocyanates, m- and p-isocyanatophenyl sulfonyl isocyanates, perchlorinated aryl polyisocyanates, polyisocyanates containing carbodiimide groups, norbornane diisocyanates, polyisocyanates containing allophanate groups, polyisocyanates containing isocyanurate groups, polyisocyanates containing urethane groups, polyisocyanates containing acrylated urea groups, polyisocyanates containing biuret groups, polyisocyanates produced by telomerization reactions, polyisocyanates containing ester groups, reaction products of the above-mentioned diisocyanates with acetals, polyisocyanates containing polymeric fatty acid esters, and mixtures thereof. Distillation residues (obtained in the commercial production of isocyanates) having isocyanate groups can also be used alone or in solution in one or more of the above-mentioned polyisocyanates.

Reactive hydrogen-containing compounds suitable for use in the foamable compositions of the present disclosure are those having at least two isocyanate-reactive hydrogen atoms, for example, in the form of hydroxyl, primary or secondary amine, carboxylic acid, or thiol groups, or a combination thereof. Polyols, i.e., compounds having at least two hydroxyl groups per molecule, due to their desirable reactivity with polyisocyanates, may be employed. Such polyols can be, e.g., polyesters, polyethers, polythioethers, polyacetals, polycarbonates, polymethacrylates, polyester amides, or hydroxyl-containing prepolymers of these compounds and a less than stoichiometric amount of polyisocyanate.

Useful polyols include ethylene glycol, 1,2- and 1,3-propylene glycol, 1,4- and 2,3-butylene glycol, 1,5-pentane diol, 1,6-hexane diol, 1,8-octane diol, neopentyl glycol, 1,4-bis(hydroxymethyl)cyclohexane, 2-methyl-1,3-propane diol, dibromobutene diol, glycerol, trimethylolpropane, 1,2,6-hexanetriol, trimethylolethane, pentaerythritol, quinitol, mannitol, sorbitol, diethylene glycol, triethylene glycol, tetraethylene glycol, higher polyethylene glycols, dipropylene glycol, higher polypropylene glycols, dibutylene glycol, higher polybutylene glycols, 4,4'-dihydroxydiphenyl propane, and dihydroxymethyl hydroquinone. Other suitable polyols include the condensation products of polybasic acids and polyols such as polyethylene adipate and polycaprolactone-based polyols, as well as the mixtures of hydroxy aldehydes and hydroxy ketones ("formose") and the polyhydric alcohols obtained therefrom by reduction ("formitol") that are formed in the autocondensation of formaldehyde hydrate in the presence of metal compounds as catalysts and compounds capable of enediol formation as co-catalysts as known in the art. Solutions of polyisocyanate polyaddition products, particularly solutions of polyurethane ureas containing ionic groups and/or solutions of polyhydrazodicarbonamides, in low molecular weight polyhydric alcohols can also be used (see DE 2,638,759).

Many other compounds containing isocyanate-reactive hydrogen atoms are useful in the preferred foamable compositions of the invention, as will be apparent to those skilled in the art of polyurethane science and technology.

Phenolic polymer precursors suitable for use in the provided foamable compositions include, for example, the reaction product of a phenol and an aldehyde in the presence of a catalyst. Illustrative uses of phenolic foams of this disclosure include use for roofing insulation, as sheathing products for external wall insulation for building applications, and for shaped parts such as pipe and block insulation for industrial applications.

The provided foamable compositions may include a nucleating agent that includes a perfluorinated aminoolefin compound as described above with respect to formula (I). The *Handbook of Polymeric Foams and Foam Technology*, Daniel Klempner and Kurt C. Frisch, ed., (Oxford University Press, 1991), discloses that formation of uniform, fine cellular structure can be obtained by using "nucleazites", also referred to as nucleating agents.

In various embodiments, the foamable compositions of the present disclosure may have a molar ratio of nucleating agent to blowing agent of no more than 1:50, 1:25, 1:9, or 1:7, 1:3, or 1:2.

Other conventional components of foam formulations can, optionally, be present in the foamable compositions of the present disclosure. For example, cross-linking or chain-extending agents, foam-stabilizing agents or surfactants, catalysts and fire-retardants can be utilized. Other possible components include fillers (e.g., carbon black), colorants, fungicides, bactericides, antioxidants, reinforcing agents, antistatic agents, and other additives or processing aids.

In some embodiments, polymeric foams can be prepared by vaporizing at least one liquid or gaseous blowing agent or generating at least one gaseous blowing agent in the presence of at least one foamable polymer or a precursor composition thereof and a nucleating agent as described above. In further embodiments, polymeric foams can be prepared using the provided foamable compositions by vaporizing (e.g., by utilizing the heat of precursor reaction) at least one blowing agent in the presence of a nucleating agent as described above, at least one organic polyisocyanate and at least one compound containing at least two reactive hydrogen atoms. In making a polyisocyanate-based foam, the polyisocyanate, reactive hydrogen-containing compound, and blowing agent composition can generally be combined, thoroughly mixed (using, e.g., any of the various known types of mixing head and spray apparatus), and permitted to expand and cure into a cellular polymer. It is often convenient, but not necessary, to preblend certain components of the foamable composition prior to reaction of the polyisocyanate and the reactive hydrogen-containing compound. For example, it is often useful to first blend the reactive hydrogen-containing compound, blowing agent composition, and any other components (e.g., surfactant) except the polyisocyanate, and to then combine the resulting mixture with the polyisocyanate. Alternatively, all components of the foamable composition can be introduced separately. It is also possible to pre-react all or a portion of the reactive hydrogen-containing compound with the polyisocyanate to form a prepolymer.

Dielectric

In some embodiments, the present disclosure is directed to dielectric fluids that include one or more a perfluorinated aminoolefin compounds of formula (I), as well as electrical devices (e.g., capacitors, switchgear, transformers, or electric cables or buses) that include such dielectric fluids. For purposes of the present application, the term "dielectric fluid" is inclusive of both liquid dielectrics and gaseous dielectrics. The physical state of the fluid, gaseous or liquid, is determined at the operating conditions of temperature and pressure of the electrical device in which it is used.

In some embodiments, the dielectric fluids include one or more perfluorinated aminoolefin compounds of formula (I) and, optionally, one or more second dielectric fluids. Suitable second dielectric fluids include, for example, air, nitrogen, nitrous oxide, oxygen, helium, argon, carbon dioxide, heptafluoroisobutyronitrile, 2,3,3,3-tetrafluoro-2-(trifluoromethoxy)propanenitrile, 1,1,1,3,4,4,4-heptafluoro-3-(trifluoromethyl)butan-2-one, $SF_6$, or combinations thereof. The second dielectric fluid may be a non-condensable gas or an inert gas. Generally, the second dielectric fluid may be used in amounts such that vapor pressure is at least 70 kPa at 25° C., or at the operating temperature of the electrical device.

The dielectric fluids of the present application are useful for electrical insulation and for arc quenching and current interruption equipment used in the transmission and distribution of electrical energy. Generally, there are three major types of electrical devices in which the dielectric fluid of the present disclosure can be used: (1) gas-insulated circuit breakers and current-interruption equipment, (2) gas-insulated transmission lines, and (3) gas-insulated transformers or (4) gas-insulated substations. Such gas-insulated equipment is a major component of power transmission and distribution systems.

In some embodiments, the present disclosure provides electrical devices, such as capacitors, comprising metal electrodes spaced from each other such that the gaseous dielectric fills the space between the electrodes. The interior space of the electrical device may also comprise a reservoir of the liquid dielectric fluid which is in equilibrium with the gaseous dielectric fluid. Thus, the reservoir may replenish any losses of the dielectric fluid.

Coating/Lubricant

In some embodiments, the present disclosure relates to coating compositions that include a solvent composition that includes one or more perfluorinated aminoolefin compounds of formula (I), and one or more coating materials which are soluble or dispersible in the solvent composition.

In various embodiments, the coating materials of the coating compositions may include pigments, lubricants, stabilizers, adhesives, anti-oxidants, dyes, polymers, pharmaceuticals, release agents, inorganic oxides, and the like, and combinations thereof. For example, coating materials may include perfluoropolyether, hydrocarbon, and silicone lubricants; amorphous copolymers of tetrafluoroethylene; polytetrafluoroethylene; or combinations thereof. Further examples of suitable coating materials include titanium dioxide, iron oxides, magnesium oxide, perfluoropolyethers, polysiloxanes, stearic acid, acrylic adhesives, polytetrafluoroethylene, amorphous copolymers of tetrafluoroethylene, or combinations thereof.

In some embodiments, the above-described coating compositions can be useful in coating deposition, where the perfluorinated aminoolefin compounds function as a carrier for a coating material to enable deposition of the material on the surface of a substrate. In this regard, the present disclosure further relates to a process for depositing a coating on a substrate surface using the coating composition. The process comprises the step of applying to at least a portion of at least one surface of a substrate a coating of a liquid coating composition comprising (a) a solvent composition containing one or more perfluorinated aminoolefin compounds as described above with respect to formula (I); and (b) one or more coating materials which are soluble or dispersible in the solvent composition. The solvent composition can further comprise one or more co-dispersants or co-solvents and/or one or more additives (e.g., surfactants, coloring agents, stabilizers, anti-oxidants, flame retardants, and the like). Preferably, the process further comprises the step of removing the solvent composition from the coating by, e.g., allowing evaporation (which can be aided by the application of, e.g., heat or vacuum).

In various embodiments, to form a coating composition, the components of the coating composition (i.e., the perfluorinated aminoolefin compound(s), the coating material(s), and any co-dispersant(s) or co-solvent(s) utilized) can be combined by any conventional mixing technique used for dissolving, dispersing, or emulsifying coating materials, e.g., by mechanical agitation, ultrasonic agitation, manual agitation, and the like. The solvent composition and the coating material(s) can be combined in any ratio depending upon the desired thickness of the coating. For example, the coating material(s) may constitute from about 0.1 to about 10 weight percent of the coating composition.

In illustrative embodiments, the deposition process of the disclosure can be carried out by applying the coating composition to a substrate by any conventional technique. For example, the composition can be brushed or sprayed (e.g., as an aerosol) onto the substrate, or the substrate can be spin-coated. In some embodiments, the substrate may be coated by immersion in the composition. Immersion can be carried out at any suitable temperature and can be maintained for any convenient length of time. If the substrate is a tubing, such as a catheter, and it is desired to ensure that the composition coats the lumen wall, the composition may be drawn into the lumen by the application of reduced pressure.

In various embodiments, after a coating is applied to a substrate, the solvent composition can be removed from the coating (e.g., by evaporation). If desired, the rate of evaporation can be accelerated by application of reduced pressure or mild heat. The coating can be of any convenient thickness, and, in practice, the thickness will be determined by such factors as the viscosity of the coating material, the temperature at which the coating is applied, and the rate of withdrawal (if immersion is utilized).

Both organic and inorganic substrates can be coated by the processes of the present disclosure. Representative examples of the substrates include metals, ceramics, glass, polycarbonate, polystyrene, acrylonitrile-butadiene-styrene copolymer, natural fibers (and fabrics derived therefrom) such as cotton, silk, fur, suede, leather, linen, and wool, synthetic fibers (and fabrics) such as polyester, rayon, acrylics, nylon, or blends thereof, fabrics including a blend of natural and synthetic fibers, and composites of the foregoing materials. In some embodiments, substrates that may be coated include, for example, magnetic hard disks or electrical connectors with perfluoropolyether lubricants or medical devices with silicone lubricants.

Direct Contact Electronic Immersion Cooling in some embodiments, the compounds of the present disclosure can be used in high value electronic cooling applications. Examples include military electronics and supercomputer applications and modern power semiconductors like Field Effect Transistors (FETs) and Insulated Gate Bipolar Transistors (IGBTs). More mainstream electronics like servers and desktop computers have historically used air cooling, but recently the demand for more computing power has caused chip powers to rise to the level that liquid cooling has begun to emerge in high performance machines, due to improved efficiency.

The perfluorinated aminoolefin compounds of formula (I), alone or in combination, may be employed as fluids for transferring heat from various electronic components by direct contact to provide thermal management and maintain optimal component performance under extreme operation conditions.

In some embodiments, the present disclosure describes the use of the perfluorinated aminoolefin compound as two-phase immersion cooling fluids for electronic devices, including computer servers.

Large scale computer server systems can perform significant workloads and generate a large amount of heat during their operation. A significant portion of the heat is generated by the operation of these servers. Due in part to the large amount of heat generated, these servers are typically rack mounted and air-cooled via internal fans and/or fans attached to the back of the rack or elsewhere within the server ecosystem. As the need for access to greater and greater processing and storage resources continues to expand, the density of server systems (i.e., the amount of processing power and/or storage placed on a single server, the number of servers placed in a single rack, and/or the number of servers and or racks deployed on a single server farm), continue to increase. With the desire for increasing processing or storage density in these server systems, the thermal challenges that result remain a significant obstacle. Conventional air cooling systems (e.g., fan based) require large amounts of power, and the cost of power required to drive such systems increases exponentially with the increase in server densities. Consequently, there exists a need for an efficient, low power usage system for cooling the servers, while allowing for the desired increased processing and/or storage densities of modern server systems.

In another embodiment, the present invention describes the use of the compounds of the present disclosure as single-phase immersion cooling fluids for electronics. Single phase immersion cooling has a long history in computer server cooling. There is no phase change in single phase immersion. Instead the liquid warms and cools as it flows or is pumped through the computer hardware and a heat exchanger, respectively, thereby transferring heat away from the server. The fluids used in single phase immersion cooling of servers typically have higher boiling temperatures exceeding about 75° C. to limit evaporative losses.

Figure 3:
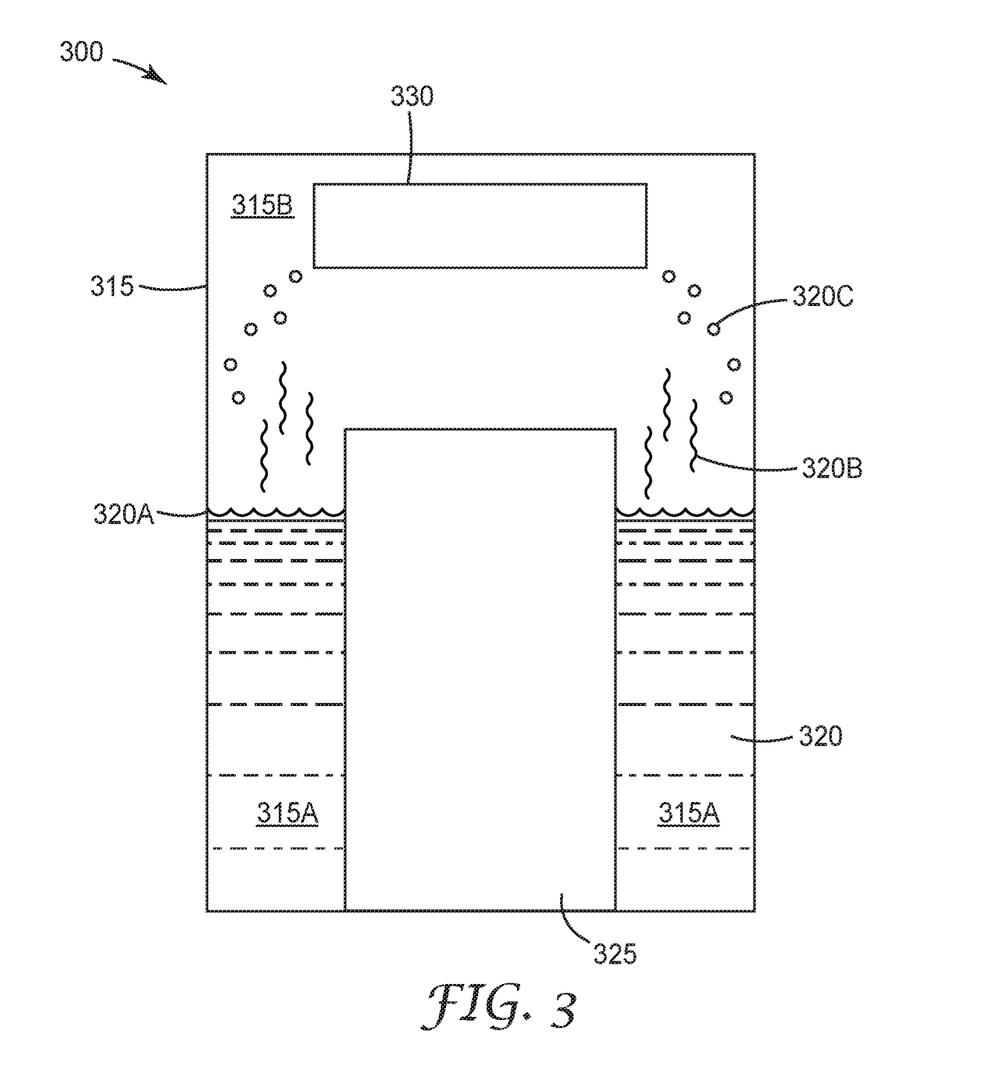
FIG. 3 is a schematic of a two-phase immersion cooling system in accordance with some embodiments of the present disclosure.

In some embodiments, the present disclosure may be directed to an immersion cooling system that includes the above-discussed perfluorinated aminoolefin-containing working fluids. Generally, the immersion cooling systems may operate as two-phase vaporization-condensation cooling vessels for cooling one or more heat generating components. As shown in FIG. 3, in some embodiments, a two-phase immersion cooling system 300 may include a housing having an interior space 315. Within a lower volume 315A of interior space 315, a liquid phase 320 of a perfluorinated aminoolefin-containing working fluid having an upper liquid surface 320A (i.e., the topmost level of the liquid phase 320) may be disposed. The interior space 315 may also include an upper volume 315B extending from the upper liquid surface 320A up to an upper portion of the housing.

In some embodiments, a heat generating component 325 may be disposed within the interior space 315 such that it is at least partially immersed (and up to fully immersed) in the liquid phase 320 of the working fluid. That is, while heat generating component 325 is illustrated as being only partially submerged below the upper liquid surface 320A, in some embodiments, the heat generating component 325 may be fully submerged below the upper liquid surface 320A. In some embodiments, the heat generating components may include one or more electronic devices, such as computer servers.

In various embodiments, a heat exchanger 330 (e.g., a condenser) may be disposed within the upper volume 315B. Generally, the heat exchanger 330 may be configured such that it is able to condense a vapor phase 320B of the working fluid that is generated as a result of the heat that is produced by the heat generating component 325. For example, the heat exchanger 330 may have an external surface that is maintained at a temperature that is lower than the condensation temperature of a vapor phase of the working fluid. In this regard, at the heat exchanger 330, a rising vapor phase 320B of the working fluid may be condensed back to liquid phase or condensate 320C by releasing latent heat to the heat exchanger 330 as the rising vapor phase 320B comes into contact with the heat exchanger 330. The resulting condensate 320C may then be returned to the liquid phase 320 disposed in the lower volume of 315A.

In some embodiments, the present disclosure may be directed to an immersion cooling system which operates by single-phase immersion cooling. Generally, the single phase immersion cooling system is similar to that of the two-phase system in that it may include a heat generating component disposed within the interior space of a housing such that it is at least partially immersed (and up to fully immersed) in the liquid phase of the working fluid. The single-phase system may further include a pump and a heat exchanger, the pump operating to move the working fluid to and from the heat generating components and the heat exchanger, and the heat exchanger operating to cool the working fluid. The heat exchanger may be disposed within or external to the housing.

While the present disclosure depicts a particular example of a suitable two-phase immersion cooling system in FIG. 3, it is to be appreciated that the benefits and advantages of the perfluorinated aminoolefin-containing working fluids of the present disclosure may be realized in any known two-phase or single-phase immersion cooling system.

In some embodiments, the present disclosure may be directed to methods for cooling electronic components. Generally, the methods may include at least partially immersing a heat electronic generating component (e.g., a computer server) in a liquid that includes the perfluorinated aminoolefins or working fluid. The method may further include transferring heat from the heat generating electronic component using the compound of the present disclosure or a working fluid comprising the compound of the present disclosure.

Direct Contact Immersion Battery Thermal Management

In some embodiments, the compounds of the present disclosure can be used as a thermal management system in electrochemical cells (e.g., lithium-ion batteries) to prevent catastrophic failure known as thermal runaway under certain conditions. Thermal runaway is a series of internal exothermic reactions that are triggered by heat. The creation of excessive heat can be from electrical over-charge, thermal over-heat, or from an internal electrical short. Internal shorts are typically caused by manufacturing defects or impurities, dendritic lithium formation and mechanical damage. While there is typically protective circuitry in the charging devices and in the battery packs that will disable the battery in the event of overcharging or overheating, it cannot protect the battery from internal shorts caused by internal defects or mechanical damage.

Direct contact fluid immersion of batteries can mitigate low probability, but catastrophic, thermal runaway events while also providing necessary ongoing thermal management for the efficient normal operation of the lithium-ion battery packs. This type of application provides thermal management when the fluid is used with a heat exchange system to maintain a desirable operational temperature range. However, in the event of mechanical damage or an internal short of any of the lithium-ion cells, the fluid would also prevent propagation or cascading of the thermal runaway event to adjacent cells in the pack via evaporative cooling, thus significantly mitigating the risk of a catastrophic thermal runaway event involving multiple cells. As with immersion cooling of electronics described above, immersion cooling and thermal management of batteries can be achieved using a system designed for single phase or two-phase immersion cooling and the fluid requirements for battery cooling are similar to those described above for electronics. In either scenario, the fluids are disposed in thermal communication with the batteries to maintain, increase, or decrease the temperature of the batteries (i.e., heat may be transferred to or from the batteries via the fluid).

Other Applications

The compounds of the present disclosure can be used in other applications. In one embodiment, the compounds of the present disclosure may be used as a monomer in polymerizations.

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Aldrich Company, Saint Louis, Mo., or may be synthesized by conventional methods.

The following abbreviations are used in this section: L=liter, mL=milliliter, sec=seconds, min=minutes, h=hours, g=gram, mol=mole, mmol=millimole, ° C.=degrees Celsius.

TABLE 1

Materials List

| DESIGNATION | Description and Source |
|---|---|
| KF | Potassium fluoride, Sigma-Aldrich, St. Louis, MO, USA |
| CsF | Cesium fluoride, Alfa Aesar, Haverhill, MA, USA |
| Satd. $NaHCO_3$ | Made by saturating sodium bicarbonate (from Alfa Aesar) in water |
| Activated carbon | Carbon, −20 + 40 mesh, Alfa Aesar |
| $K_2CO_3$ | Potassium carbonate, Alfa Aesar |
| Molecular sieves | 4 Angstrom molecular sieves, Sigma-Aldrich |
| $SiO_2$ | Silica gel, Sigma-Aldrich |
| Basic alumina | Basic alumina, Alfa Aesar |
| Diglyme | Diethylene glycol dimethyl ether, Sigma-Aldrich |
| Tetraglyme | Tetraethylene glycol dimethyl ether, Alfa Aesar |
| NMP | N-Methyl-2-pyrrolidinone, Sigma-Aldrich |
| 2,2,3,3,5,6,6-Heptafluoro-1,4-oxazine | Material can be prepared by following the method described in Dalton Transactions 2011, 40, 8569-8580; V. K. Grinevskaja, et al. |
| 2,2,3,3,4,4,5-Hepta-fluoropyrrole | Fluorine Notes 2009, 63; or Izvestiya Akademii Nauk SSSR, Seriya Khimicheskaya 1984, 33, 1711-1714. |
| Dimethylamino imine | Material can be prepared by following methods described in Inorg. Chem. 1990, 29, 571-572. |
| Perfluorocyclohexene | Perfluorocyclohexene, SynQuest Laboratories, Inc., Alachua, FL, USA |
| Perfluorocyclopentene | Perfluorocyclopentene, abcr GmbH, Karlsruhe, Germany |
| Perfluoro-2-butene | Perfluoro-2-butene, SynQuest Laboratories, Inc. |
| Perfluoro-2-pentene | Material can be prepared by following methods described previously. See: Journal of Fluorine Chem. 1985, 417-423. |
| FC-43 | Engineered fluid obtained under the trade designation "3M FLUORINERT ELECTRONIC LIQUID FC-43", 3M Company, Maplewood, MN, USA. |
| FC-70 | Engineered fluid obtained under the trade designation "3M FLUORINERT ELECTRONIC LIQUID FC-70", 3M Company |
| FC-71 | Engineered fluid available under the trade designation "3M FLUORINERT ELECTRONIC LIQUID FC-71", 3M Company |
| Adogen 464 | Methyltrialkyl($C_8$-$C_{10}$)ammonium chloride, Sigma Aldrich |

Test Methods

Gas Chromatography with Flame Ionization Detector (GC-FID) Test Method

GC-FID analysis was carried out on an Agilent Technologies 7890B GC System (Santa Clara Calif.) equipped with a Restek RtX-200 gas chromatography column (Bellefonte, Pa.) and helium carrier gas. Once material was injected into the column, the following temperature sequence was executed: 5 min hold at 40° C., 10° C./minute temperature increase over the span of 21 min to reach a final temperature of 250° C., and then a 15 min hold at 250° C. Data analysis by use of Agilent Open LAB CDSA ChemStation software enabled the determination of product purities and GC yields.

Preparatory Example 1 (PE-1): Preparation of 2,2,3,3,4,4,5,5-octafluoro-1-(perfluorocyclohex-1-en-1-yl)pyrrolidine

To a 300 mL Hastelloy reaction vessel were added CsF (6.8 g, 45 mmol) and diglyme (80 mL). The resultant mixture was stirred at room temperature (25° C.) and charged with perfluorocyclohexene (30.1 g, 115 mmol) over the course of 30 min with no observed temperature rise. To the resultant mixture was then added 2,2,3,3,4,4,5-heptafluoropyrrole (27.1 g, 139 mmol). After a 30 min stir, the reaction mixture temperature was slowly raised to 65° C. After a 2 hour stir, the resultant reaction mixture was heated to 80° C. and allowed to stir overnight at the same temperature. The mixture was then allowed to cool to room temperature (25° C.) followed by the addition of water and satd. NaHCO$_3$—The fluorous phase was separated, collected, and analyzed by GC-FID, which indicated complete conversion of the 2,2,3,3,4,4,5-heptafluoropyrrole starting material. The crude fluorous phase was distilled by concentric tube distillation affording 2,2,3,3,4,4,5,5-octafluoro-1-(perfluorocyclohex-1-en-1-yl)pyrrolidine (139° C./740 mmHg, 47 g, 65% isolated yield) as a colorless liquid. Gas chromatography with mass spectrometry (GC-MS) and $^{19}$F nuclear magnetic resonance (NMR) analyses confirmed the isolated compound to be that of the desired 2,2,3,3,4,4,5,5-octafluoro-1-(perfluorocyclohex-1-en-1-yl)pyrrolidine.

Preparatory Example 2 (PE-2): Preparation of 2,2,3,3,4,4,5,5-octafluoro-1-(perfluorocyclopent-1-en-1-yl)pyrrolidine

To a 300 mL Hastelloy reaction vessel were added CsF (7.2 g, 47 mmol) and diglyme (66 mL). The resultant mixture was then charged with perfluorocyclopentene (32.2 g, 152 mmol) with stirring. No temperature rise was observed. To the resultant mixture was charged 2,2,3,3,4,4,5-heptafluoropyrrole (30.6 g, 157 mmol) over the course of 30 min. After complete addition followed by an additional 30 min stir, the reaction temperature was slowly raised to 60° C. After a 2 day stir at the same temperature, the mixture was allowed to cool to room temperature (25° C.) with stirring followed by the addition of water (100 mL). The fluorous phase was separated, collected, and analyzed by GC-FID which indicated complete conversion of the 2,2,3,3,4,4,5-heptafluoropyrrole starting material. The fluorous phase was purified via single-plate distillation affording 2,2,3,3,4,4,5,5-octafluoro-1-(perfluorocyclopent-1-en-1-yl)pyrrolidine (114° C./740 mmHg, 50.2 g, 71% isolated yield) as a colorless liquid. GC-MS and $^{19}$F NMR analyses confirmed the isolated compound to be that of the desired 2,2,3,3,4,4,5,5-octafluoro-1-(perfluorocyclohex-1-en-1-yl)pyrrolidine.

Preparatory Example 3 (PE-3): Preparation of 2,2,3,3,5,5,6,6-octafluoro-4-(perfluorocyclopent-1-en-1-yl)morpholine To a 600 mL stainless steel reaction vessel were charged CsF (25.8 g, 170 mmol) and diglyme (159 mL). The reactor was sealed and then evacuated under reduced pressure. The evacuated reaction vessel was then charged with perfluorocyclopentene (90.1 g, 425 mmol) To the resultant stirring reaction mixture was charged 2,2,3,3,5,6,6-heptafluoro-1,4-oxazine (107.8 g, 511 mmol) over the course of 30 min with an observed internal temperature rise to 38° C. The resultant reaction mixture was then slowly heated to 80° C. followed by a 16 h stir at the same temperature. To the resultant reaction mixture was added water (250 mL). The fluorous phase was separated, collected, and analyzed by GC-FID which indicated complete conversion of the 2,2,3,3,4,4,5-heptafluoropyrrole starting material. The fluorous phase was purified via concentric tube distillation affording 2,2,3,3,5,5,6,6-octafluoro-4-(perfluorocyclopent-1-en-1-yl)morpholine (129° C./740 mmHg, 141.3 g, 79% isolated yield) as a colorless liquid. 19F NMR analysis confirmed the isolated compound to be that of the desired 2,2,3,3,5,5,6,6-octafluoro-4-(perfluorocyclopent-1-en-1-yl)morpholine

Preparatory Example 4 (PE-4): Preparation of 2,2,3,3,4,4,5,5-octafluoro-1-(perfluoropent-2-en-3-yl)pyrrolidine and 2,2,3,3,4,4,5,5-octafluoro-1-(perfluoropent-2-en-2-yl)pyrrolidine To a 300 mL Hastelloy reaction vessel were added CsF (7.8 g, 51 mmol) and diglyme (69 g, 514 mmol). The resultant mixture was evacuated under reduced pressure and then charged with perfluoropent-2-ene (32 g, 128 mmol) with stirring and without any observed increase in temperature. 2,2,3,3,4,4,5-Heptafluoropyrrole (25.0 g, 128 mmol) was added to the resultant mixture. After complete addition, the reaction temperature was slowly raised to 60° C. After an overnight stir at the same temperature, the reaction mixture was allowed to cool to room temperature (25° C.) followed by the addition of water (100 mL). The fluorous layer was analyzed by GC-FID and showed complete conversion of the 2,2,3,3,4,4,5-heptafluoropyrrole starting material. The fluorous phase was purified via single-plate distillation affording 2,2,3,3,4,4,5,5-octafluoro-1-(perfluoropent-2-en-2-yl)pyrrolidine (125° C./740 mmHg, 9.9 g, 18% isolated yield) as a colorless liquid. GC-MS analysis confirmed the isolated compound to be that of the desired 2,2,3,3,4,4,5,5-octafluoro-1-(perfluoropent-2-en-2-yl)pyrrolidine.

Preparatory Example 5 (PE-5): Preparation of 2,3,3,4,4,5,5-heptafluoro-N,N-bis(trifluoromethyl)cyclopent-1-en-1-amine To a 300 mL Hastelloy reaction vessel were added CsF (7.23 g, 47.6 mmol) and diglyme (42.5 mL). The reaction vessel was then sealed, evacuated under reduced pressure, and slowly heated to 70° C. with stirring. To the resultant mixture was charged 1,1-difluoro-N-(trifluoromethyl)methanimine (16.0 g, 120 mmol) in 1 g batch-charges over the course of 2 hours. The resultant reaction mixture was allowed to stir for 16 h at the same temperature. The reaction mixture was then allowed to cool to room temperature (25° C.) followed by the addition of water (50 mL). The fluorous layer was analyzed by GC-FID and showed a peak indicative of the desired 2,3,3,4,4,5,5-heptafluoro-N,N-bis(trifluoromethyl)cyclopent-1-en-1-amine (3% purity by uncorrected GC-FID yield). The structure was confirmed by GC-MS analysis to be that of the desired 2,3,3,4,4,5,5-heptafluoro-N,N-bis(trifluoromethyl)cyclopent-1-en-1-amine.

Preparatory Counter—Example 1 (PCE-1): Attempted Preparation of 1,1,1,4,4,5,5,5-octafluoro-3-((perfluoropropan-2-yl)oxy)-2-(trifluoromethyl)pent-2-ene by CsF Catalyzed Reaction of 1,1,1,3,4,4,5,5,5-nonafluoro-2-(trifluoromethyl)pent-2-ene with Hexafluoroacetone

In this synthesis an attempt was made to add the olefinic C—F bond of 1,1,1,3,4,4,5,5,5-nonafluoro-2-(trifluoromethyl)pent-2-ene across the CO═double bond of hexafluoroacetone using CsF as catalyst, in analogy with the additions olefinic C—F bonds across the C═N double bond of imines described in the preparatory examples of the present disclosure.

To a 300 mL Hastelloy Parr reaction vessel were added anhydrous CsF (3.104 g, 20.4 mmol), anhydrous diglyme (80.8 g), anhydrous sulfolane (21.0 g), and 1,1,1,3,4,4,5,5,5-nonafluoro-2-(trifluoromethyl)pent-2-ene (54.63 g, 182.1 mmol). The reactor was immediately sealed and the resultant mixture was chilled to less than −50 C in a dry ice bath, evacuated to less than 1 Torr using a vacuum pump, and then batch charged with hexafluoroacetone (34.40 g, 207.2 mmol) from a lecture bottle. Once addition was complete, the Parr reactor was mounted in a reactor stand equipped with mechanical overhead stirrer and heating mantle. Stirring at 1000 revolutions per min was begun and the reaction temperature was slowly raised to 70° C. over a period of 3 hrs and then held at 70° C. for 1.5 hrs before allowing reaction mixture to cool overnight to room temperature (28° C.). The following morning, residual pressure was vented from the reactor at room temperature, the reactor was chilled in a dry ice bath to less than −40° C. and briefly evacuated and then charged with 100 mL of water by suction to quench the reaction mixture. After warming to room temperature and stirring, the reactor was disassembled and the reaction mixture was transferred to a separatory funnel and the lower fluorous layer (42.95 g) was isolated and analyzed by GC-FID. GC analysis revealed the presence of unreacted 1,1,1,3,4,4,5,5,5-nonafluoro-2-(trifluoromethyl)pent-2-ene (85.6 area %) and 1,1,1,2,2,3,3,5,5,5-decafluoro-4-(trifluoromethyl)pentane 11.73% as the only significant components in the isolated fluorous phase. No evidence of the desired addition product with hexafluoroacetone was detected by GC-FID. The results indicate that addition of the olefinic C—F bond of 1,1,1,3,4,4,5,5,5-nonafluoro-2-(trifluoromethyl)pent-2-ene across the C═O double bond of hexafluoroacetone does not occur under these reaction conditions, contrary to the surprising reactivity of perfluorinated imines with perfluoroolefins described in the present disclosure.

Preparatory Counter—Example 2 (PCE-2): Preparation of 2,2,3,3,6,6-hexafluoro-5-[1,2,2,2-tetrafluoro-1-(trifluoromethyl)ethyl]-1,4-oxazine In this experiment an attempt was made to add the olefinic C—F bond of 1,1,2,3,3,3-hexafluoropropene across the C═N double bond of 2,2,3,3,5,6,6-Heptafluoro-1,4-oxazine using KF as catalyst, in analogy with the additions of other olefinic C—F bonds across the C═N double bond of imines described in the preparatory examples of the present disclosure.

To a 600 mL stainless steel reaction vessel were charged KF (6.0 g, 103 mmol), diglyme (130 g), Adogen 464 (1 g, 2.1 mmol) and 2,2,3,3,5,6,6-heptafluoro-1,4-oxazine (51.3 g, 243.3 mmol.) The reactor was sealed and heated to 70° C. Hexafluoropropene (54.7 g, 365 mmol) was added over a period of about 2 hours. The reaction mixture was held at 70° C. for 16 hours and then cooled to room temperature. The reaction vessel was emptied and the reaction was repeated using KF (8.0 g, 138 mmol), diglyme (150 g), Adogen 464 (1 g, 2.1 mmol), 2,2,3,3,5,6,6-heptafluoro-1,4-oxazine (150 g, 711 mmol) and hexafluoropropene (160 g, 1066 mmol). The two reaction mixtures were combined and added to a separatory funnel. The lower phase was water washed, dried with magnesium sulphate and filtered to provide 300 grams of material which was purified by fractionation using at 15-tray vacuum jacketed Oldershaw column to provide 132.6 grams of 2,2,3,3,6,6-hexafluoro-5-[1,2,2,2-tetrafluoro-1-(trifluoromethyl)ethyl]-1,4-oxazine with a purity of >98.5% with a boiling point of about 80° C. The structure was confirmed by GC-MS and $^{19}F$ NMR analyses. The results indicate that addition of certain olefinic C—F bonds, such as 1,1,2,3,3,3-hexafluoropropene, across the C=N double bond of hexafluoroacetone does not occur under these reaction conditions, contrary to the addition of perfluorocyclopentene and perfluorocyclohexene olefinic C—F bonds across C=N of perfluorinated imines described in the present disclosure.

Physical Properties:

Thermal Stability of PE-1

Thermal stability was measured by charging 1.0 g of PE-1 into glass vials and then adding a weighed amount of absorbent. The samples were stirred for 24 hours at 60° C., allowed to cool, and then analyzed by GC-FID for decomposition and purity changes. The thermal stability testing results with various absorbents are shown in the Table 2.

TABLE 2

Thermal Stability of PE-1.

| | No Absorbent | Activated Carbon | 4 Angstrom Molecular Sieves | $K_2CO_3$ | Basic Alumina | Silica Gel |
|---|---|---|---|---|---|---|
| Purity, % | 97.7 | 97.7 | 97.3 | 97.6 | 97.6 | 97.7 |

Pour Point Data for PE-1, PE-2, PE-3, and PE-4

Pour points of PE-1, PE-2, PE-3, and PE-4 were determined visually and defined as the lowest temperature at which the sample was observed to flow within 5 sec while being held horizontally. 102 mL of the sample was placed in a vial and cooled in a liquid nitrogen-cooled pentane bath until it solidified. The sample was then allowed to warm slowly in the pentane bath by removal of the liquid nitrogen cooling source (typically an increase of 1-2° C./minute) and observed every 3-5° C. The pour point for each of the samples is summarized in Table 3.

TABLE 3

Pour Point Data.

| PE-1 | PE-2 | PE-3 | PE-4 |
|---|---|---|---|
| −34° C. | −33° C. | −49° C. | −90° C. |

Atmospheric Lifetime and Global Warming Potential (GWP) of PE-1

The atmospheric lifetime of PE-1 was determined from its rate of reaction with hydroxyl radicals. The pseudo-first order rates for the reaction of gaseous PE-1 with hydroxyl radical was measured in a series of experiments relative to reference compounds such as chloromethane and ethane. The measurements were performed in a 5.7 L, heated Fourier-transform infrared (FTIR) gas cell equipped with a polished semiconductor-grade quartz window. An ORIEL Instruments UV Lamp, Model 66921 (Newport Corporation, Irvine, Calif., USA) equipped with a 480 W mercury-xenon bulb was used to generate hydroxyl radicals by photolyzing ozone in the presence of water vapor. The concentrations of PE-1 and the reference compound were measured as a function of reaction time using an I-Series FTIR from Midac Corporation (Westfield, Mass., USA). The atmospheric lifetimes were calculated from the reaction rates for PE-1 relative to the reference compounds and the reported lifetime of the reference compounds as shown below:

$$\tau_x = \tau_r \cdot \frac{k_r}{k_x}$$

where $\tau_x$ is the atmospheric lifetime of PE-1, $\tau_r$ is the atmospheric lifetime of the reference compound, and $k_x$ and $k_r$ are the rate constants for the reaction of hydroxyl radical with the PE-1 and the reference compound, respectively. It was found that the atmospheric lifetime of PE-1 is 5.0 years.

Global warming potential (GWP) was estimated for PE-1 using the atmospheric lifetime. The GWP was calculated according to the Intergovernmental Panel on Climate Change (IPCC) 2013 method using a 100 year integration time horizon (ITH). The radiative efficiencies used in this calculation were based upon the infrared cross-sections measured on PE-1. It was found that PE-1 has a GWP of 416. In comparison, for saturated perfluorocarbons, saturated perfluorocarbons typically have a GWP of greater than 5000.

Dielectric Constant of PE-1, FC-43 (CE-1), and FC-70 (CE-2), and FC-71 (CE-3)

The dielectric constant (tested per ASTM D150-11) of PE-1 was measured. The dielectric constant measured at 1 kHz was 1.98. The dielectric constant is comparable to FC-43 (1.9), FC-70 (1.98), and FC-71 (1.97).

All cited references, patents, and patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. A perfluorinated aminoolefin compound represented by the following general formula (I): CFY=CXN($R_f$)$CF_2R_f'$ where:
    (a) $R_f$ and $R_f'$ are (i) independently selected from a linear or branched perfluoroalkyl group having 1-8 carbon atoms, optionally comprising at least one catenated O or N atom, or (ii) bonded together to form a perfluorinated ring structure having 4-8 ring carbon atoms, optionally comprising at least one catenated O atom; and (b) X and Y are (i) independently selected from a perfluoroalkyl group having 1-4 carbon atoms, or (ii) bonded together to form a perfluorinated ring structure having 5-6 ring carbon atoms.

2. The compound according to claim 1, wherein $R_f$ and $R_f'$ are bonded together to form a five- or six-membered ring.

3. The compound according to claim 1, wherein the perfluorinated ring structure having 4-8 ring carbon atoms further comprises at least one perfluorinated alkyl substituent.

4. The compound according to claim 1, wherein $R_f$ and $R_f'$ are independently selected from —$CF_3$, —$CF_2CF_3$, or —$CF_2CF_2CF_3$.

5. The compound according to claim 1, wherein X and Y are bonded together to form a 5-membered ring.

6. The compound according to claim 1, wherein the perfluorinated ring structure having 5-6 ring carbon atoms further comprises at least one perfluorinated alkyl substituent.

7. The compound according to claim 1, wherein X and Y is —$CF_3$.

8. The compound according to claim 1, wherein (i) X is —$CF_3$ and Y is —$CF_2CF_3$ or (ii) X is —$CF_2CF_3$ and Y is —$CF_3$.

9. The compound of claim 1, wherein the perfluorinated aminoolefin compound is at least one of:

10. The compound of claim 1, wherein the perfluorinated aminoolefin compound is at least one of:

-continued

[chemical structures showing perfluorinated aminoolefin compounds with morpholine, azepane rings, and various N-substituted groups including N—CF₃, N—CF₂CF₃, N(CF₂CF₃)₂, and N(CF₂CF₂CF₃)₂]

11. The compound of claim 1, wherein the perfluorinated aminoolefin compound has a dielectric constant of less than 2.3.

12. The compound of claim 1, wherein the perfluorinated aminoolefin compound has a pour point of less than −30° C.

13. A foamable composition comprising:
   a blowing agent;
   a foamable polymer or a precursor composition thereof; and
   a nucleating agent, wherein said nucleating agent comprises the perfluorinated aminoolefin compound according to claim 1.

14. An apparatus for converting thermal energy into mechanical energy in a Rankine cycle comprising:
   a working fluid;
   a heat source to vaporize the working fluid and form a vaporized working fluid;
   a turbine through which the vaporized working fluid is passed thereby converting thermal energy into mechanical energy;
   a condenser to cool the vaporized working fluid after it is passed through the turbine; and
   a pump to recirculate the working fluid,
   wherein the working fluid comprises the perfluorinated aminoolefin compound according to claim 1.

15. An immersion cooling system comprising:
   a housing having an interior space;
   a heat-generating component disposed within the interior space; and
   a working fluid liquid disposed within the interior space such that the heat-generating component is in contact with the working fluid liquid;
   wherein the working fluid comprises the perfluorinated aminoolefin compound according to claim 1.

16. A thermal management system for a lithium-ion battery pack comprising:
   a lithium-ion battery pack; and
   a working fluid in thermal communication with the lithium-ion battery pack;
   wherein the working fluid comprises the perfluorinated aminoolefin compound according to claim 1.

17. The system according to claim 16, wherein the perfluorinated aminoolefin compound is present in the working fluid at an amount of at least 25% by weight based on the total weight of the working fluid.

18. A thermal management system for an electronic device, the system comprising:
   an electronic device selected from a microprocessor, a semiconductor wafer used to manufacture a semiconductor device, a power control semiconductor, an electrochemical cell, an electrical distribution switch gear, a power transformer, a circuit board, a multi-chip module, a packaged or unpackaged semiconductor device, a fuel cell, or a laser; and
   a working fluid in thermal communication with the electronic device;
   wherein the working fluid comprises the perfluorinated aminoolefin compound according to claim 1.

19. A working fluid comprising the perfluorinated aminoolefin compound according to claim 1, wherein the unsaturated fluorinated compound is present in the working fluid in an amount of at least 5% by weight based on the total weight of the working fluid.

20. An apparatus for heat transfer comprising:
   a device; and
   a mechanism for transferring heat to or from the device, the mechanism comprising a heat transfer fluid that comprises the perfluorinated aminoolefin compound according to claim 1.

* * * * *